(12) United States Patent
Iiyama et al.

(10) Patent No.: US 6,835,066 B2
(45) Date of Patent: Dec. 28, 2004

(54) PROCESS FOR PREPARING DENTAL PROSTHESIS

(75) Inventors: Kenichi Iiyama, Tokyo (JP); Tatsuru Doumoto, Tokyo (JP); Yuki Sakamoto, Tokyo (JP)

(73) Assignee: GC Corporation, Tokyo (JP)

(*) Notice: Subject to any disclaimer, the term of this patent is extended or adjusted under 35 U.S.C. 154(b) by 54 days.

(21) Appl. No.: 10/050,956

(22) Filed: Jan. 22, 2002

(65) Prior Publication Data

US 2002/0102520 A1 Aug. 1, 2002

(30) Foreign Application Priority Data

Jan. 31, 2001 (JP) ........................................ 2001-024128

(51) Int. Cl.⁷ ................................................. A61C 5/10
(52) U.S. Cl. ........................................ 433/223; 433/215
(58) Field of Search ................................ 433/215, 223, 433/213, 214

(56) References Cited

U.S. PATENT DOCUMENTS 4,742,464 A  *  5/1988  Duret et al.
5,121,333 A  *  6/1992  Riley et al.
5,273,429 A  * 12/1993  Rekow et al. ............... 433/215
5,440,496 A  *  8/1995  Andersson et al.
5,452,219 A  *  9/1995  Dehoff et al.
5,851,115 A  * 12/1998  Carlsson et al.
6,126,445 A  * 10/2000  Willoughby ................. 433/223

FOREIGN PATENT DOCUMENTS

WO     WO 96/37163     11/1996
WO     WO 98/51232     11/1998

\* cited by examiner

*Primary Examiner*—Ralph A. Lewis
(74) *Attorney, Agent, or Firm*—Oblon, Spivak, McClelland, Maier & Neustadt, P.C.

(57) ABSTRACT

A measuring center stores three-dimensional coordinate information of an intra-oral shape measured by impression taking as a digital signal. The measuring center sends the obtained measured data to a design center using communication apparatus. The design center reproduces the intra-oral shape on a graphic display device based on the received measuring data as a three-dimensional graphic, designs a shape of a dental prosthesis and stores it as a digital signal. The processing center transmits the received design data to a milling processor as a processing command and subjects a block material to milling processing to prepare a dental prosthesis.

1 Claim, No Drawings

PROCESS FOR PREPARING DENTAL PROSTHESIS

BACKGROUND OF THE INVENTION

1. Field of the Invention

The present invention relates to a process for preparing a dental prosthesis such as an inlay, a crown, and a bridge utilizing a CAD/CAM (computer-aided design and manufacturing) apparatus. In particular, the present invention relates to a process for preparing a dental prosthesis comprising carrying out the design of a dental prosthesis at a design center where dental technicians having an expert knowledge for a CAD design are employed, by sending and receiving of a data utilizing communication means.

2. Description of the Conventional Art

Hitherto, for the preparation of dental prostheses such as inlays, crowns, and bridges, there has been generally employed a process in which a metal material or a ceramics material is cast by the lost wax casting process. Further, dental prostheses, in which the principal object is placed at aesthetics, such as ceramic inlays and all-ceramic crowns, are prepared by building up a porcelain on a refractory casting material and firing it in a vacuum electric furnace.

Usually, the preparation of dental prostheses by the lost wax casting process is carried out in the following procedures. That is, a prosthesis shape to be restored is prepared using a wax on a plaster model prepared by pouring a gypsum into an impression obtained by impression taking within an oral cavity, followed by setting; the obtained wax pattern is invested in a refractory investment; after setting the investment, the assembly is placed in an electric furnace and heated to burn the wax pattern; a metal or a ceramics material is cast in the obtained casting mold; and after cooling, the cast material is excavated from the investment, cut and polished to prepare a desired dental prosthesis such as an inlay and a crown. Further, in the case of ceramic inlays, all-ceramic crowns and the like, they are prepared in a process in which a duplicated cast is prepared using a refractory casting material; a porcelain is built up on the duplicated cast to form a desired dental prosthesis shape; and after firing in a vacuum firing furnace, the refractory casting material is removed, followed by forming the surface characterization and polishing.

Since the state of a dental caries and the intra-oral shape vary in patients one by another, a dental prosthesis to be prepared is also different in the patients one by another. Accordingly, the form of the dental prosthesis is designed and prepared based on intuition and experiences of a dental technician while taking into account the relation with antagonists or adjacent teeth or the occlusal relation. Moreover, as described above, the operation for preparing the dental prosthesis is complicated and includes many steps of manual works. Nonetheless, the completed prosthesis is required to have an extremely high dimensional precision in the order of several $\mu$m. Thus, required are not only a skill of the dental technician, but also a long period of time and labors.

Under these circumstances, as a method for supplying dental prostheses having a constant quality within a short period of time stably and in a large quantity, in recent years, a CAD/CAM (computer-aided design and manufacturing) system in which a dental prosthesis such as an inlay, a crown and a bridge is designed on a screen utilizing a computer and prepared by milling processing is paid attention. Particularly, a design and preparation system of a dental prosthesis using a CAD/CAM system represented by the Cerec system (a system of Siemens AG, Germany) has been paid attention. This CAD/CAM system is a process in which the shape of a tooth subjected to preparation of abutment tooth or cavity preparation and if necessary, the shapes of adjacent teeth or antagonists are read out; a desired dental prosthesis is designed based on the thus read out tooth shape using a computer; and a block-like material such as a resin cured material, a ceramic sintered material, and a metal material is set in an automatic milling processor and subjected to milling processing to prepare the desired dental prosthesis.

In comparison with the casting process as described above, this CAD/CAM system is characterized in that dental prostheses can be prepared with good efficiency; if the design is properly carried out, the completed dental prostheses are high in the precision; and that dental prostheses having superior fitness precision in an oral cavity can be prepared. According to the CAD/CAM system, it is possible to undergo the computation for determining the ultimate shape of the dental prosthesis (converting the shape into information for processing) through automatic computation by a computer. However, since the state of a dental caries and the intra-oral shape vary in patients one by another, it is necessary to carry out ultimately the design for ideally forming a shape of a dental prosthesis as its basis in a manual manner. In order to design and determine the shape of this dental prosthesis, required are not only a knowledge and technique of a skilled dental technician based on an anatomical shape of the tooth, but also a knowledge and technique for a design operation of highly advanced CAD. It is difficult to prepare an ideal dental prosthesis having a superior fitness precision because of difficulty of the design operation. This matter is one of the causes to inhibit the diffusion of the CAD/CAM system.

In addition, a major part of the current dental prostheses are prepared by the lost wax casting process. Accordingly, with respect to the preparation process of dental prostheses by the lost wax casting process, thorough educations are given in schools for dental technicians and the like. On the other hand, it is the present situation that educations regarding the preparation process of dental prostheses using a CAD/CAM system are scarcely given. For this reason, even when a dental laboratory employs a CAD/CAM apparatus, it is very difficult for a dental technician who, it is hard to say, has a sufficient knowledge and technique for CAD, to design an ideal dental prosthesis. Further, it is the present situation that the dimensional precision and fitness precision of the completed dental prosthesis are not so good as expected and that the preparation efficiency is not so superior as expected. Moreover, according to the CAD/CAM system that has hitherto been employed, it is required to set up all implements for the measurement, design and processing in one place, and the implements are expensive. Accordingly, it is the present situation that it is hard to say that the preparation process of a dental prosthesis utilizing the CAD/CAM system is diffused into general dental laboratories, except for large dental laboratories or dental offices.

SUMMARY OF THE INVENTION

Then, the present invention is aimed to overcome the difficulty in designing a dental prosthesis, which is the most fatal problem of the conventional art process for preparing a dental prosthesis by the CAD/CAM system as described above, and provide a process for preparing a dental prosthesis, enabling to supply dental prostheses having a constant quality within a short period of time stably and in a large quantity, the dental prostheses thus prepared being good in the precision and superior in the intra-oral fitness, an aspect of which is the original purpose of the CAD/CAM system.

In order to achieve the above-described aim, we, the present inventors, made extensive and intensive investigations. As a result, it has been found that a data obtained by measuring an intra-oral shape at a measuring center of a dental laboratory, a dental office, etc. is sent to a design center utilizing communication means; the design center where an expert having a skilled knowledge and technique for dental techniques as well as having a sufficient knowledge and technique for a CAD design is employed, is in charge of a design stage of a dental prosthesis, which is the most difficult in the CAD/CAM system, thereby carrying out concentrically the design of an ideal dental prosthesis; the design data taken by the expert is then sent to a processing center utilizing communication means and inputted into a CAM apparatus; and milling processing is carried out, whereby the resulting dental prosthesis is fitted within an oral cavity of a patient quite well, and thus, the preparation of a dental prosthesis utilizing a CAD/CAM system can be carried out efficiently, leading to accomplishment of the present invention.

Specifically, the process for preparing a dental prosthesis according to the present invention is a process for preparing a dental prosthesis utilizing a CAD/CAM system, which is characterized in that a measuring center stores three-dimensional coordinate information of an intra-oral shape measured on a basis of a plaster model prepared by impression taking within an oral cavity of a patient, or an intra-oral shape measured on a basis of an image taken by photographing within an oral cavity of a patient, as a digital signal and sends the obtained measure data to a design center using communication means; the design center reproduces the intra-oral shape on a graphic display device based on the received measure data by means of a three-dimensional graphic, designs a shape of a dental prosthesis and stores it as a digital signal, and then sends the obtained design data of the dental prosthesis to a processing center using communication means; and the processing center transmits the received design data to a milling processor as a processing command and subjects a block material to milling processing to prepare a dental prosthesis.

DESCRIPTION OF THE PREFERRED EMBODIMENTS

The process for preparing a dental prosthesis according to the present invention is carried out in the following manner. That is, first of all, an interior of an oral cavity (tooth shape or dentition shape) of a patient is subjected to impression taking using a dental impression material in a dental office or the like, to prepare a plaster model. For example, in the case where a No. 6 crown in the left side of a mandibula of a patient is prepared using a resin material, a dentition shape of a formed abutment tooth (No. 6 in the left side of the mandibula), and its adjacent teeth (Nos. 5 and 7 in the left side of the mandibula) and a dentition shape of antagonists (a dentition in a counterpart relation with an objective side, such as Nos. 5 to 7 in the left side of the maxilla) are subjected to impression taking using a precise impression material such as a dental silicone impression material, and respective sectional and removable type plaster models are prepared using a dental gypsum based on the thus taken impression. Here, as the abutment tooth, included are not only the case of one prepared by cutting and forming a crown or root portion of a natural tooth, but also the case where a lower structure of a dental prosthesis fixed in an intra-oral side of an implant fixture embedded within a mandible of a deficient tooth portion is fixedly adhered.

Next, a measuring center, which is provided with a measuring instrument capable of measuring a three-dimensional coordinate of the prepared plaster model, measures a three-dimensional coordinate of the plaster model, stores it as a digital signal, and sends the obtained measuring data to a design center using communication means. Here, the measuring center, which is provided with a measuring instrument capable of measuring a three-dimensional coordinate, generally means dental laboratories, dental offices, and the like.

At the measuring center, the abutment tooth portion of the sectional and removable plaster model is fixed on a measuring table using a dental utility wax, etc., and three-dimensional coordinate information of the abutment tooth is measured using a measuring instrument. Then, three-dimensional coordinate information regarding the dentition shape in the abutment tooth side and the dentition shape in the antagonist side is measured. At this time, with respect to the positional relation of dentitions of upper and lower jaws, it is preferred that reference points are previously provided during measuring the plaster models of the upper and lower jaws, and both the reference points of the information as measured for the plaster model of the maxillary dentition and the information as measured for the plaster model of the mandibular dentition are then made to coincide, thereby enabling to subject the positional relation of the dentitions of the upper and lower jaws to graphic display. Incidentally, when a non-contact type measuring instrument is used as the measuring instrument for measuring the three-dimensional coordinate information of the abutment tooth, its use does not hinder the case where the plaster model is re-used, or it is returned to a dental office or the like and used later as a reference data by the dental office or the like. Thus, such is preferred.

As the non-contact type measuring instrument, used is preferably a laser type measuring instrument. In the case where the laser type measuring instrument is used, when the plaster model is colored black, the scatter of the laser beams can be reduced, and hence, such is preferred. After completion of the measurement of the shape of the plaster model, the obtained three-dimensional coordinate information is stored in a memory within a computer, or an external preservation medium such as a floppy disc and an MO (magneto-optical) disc, as a digital signal.

On the other hand, as the method for obtaining three-dimensional coordinate information of an intra-oral shape as measured based on images taken by photographing an interior of an oral cavity of a patient, first of all, the interior of the oral cavity of the patient is photographed using an intra-oral camera as generally employed in a dental office or the like, in various directions to the objective tooth, to photograph a plurality of images (preferably, from 5 to 6 pieces of images). Next, the measuring center, which is provided with a measuring instrument, carries out the measurement by conversion processing into a three-dimensional data using a computer on a basis of these images, to obtain three-dimensional coordinate information regarding the intra-oral shape.

The thus obtained measuring data is sent to a design center from the measuring center utilizing communication means such as E-mail and Internet. During the communication of the measuring data, information regarding the name, age, intra-oral photograph and identification number of a patient is also communicated simultaneously, in addition to the measuring data of an intra-oral site of the patient. It is preferred that codes and the like are imparted to these measure information, thereby protecting the privacy of the patient. Further, it is preferred that setting is made such that a prearranged date for return of a design data from the design center who has received the measure data is automatically noticed, upon sending the measure data to the design center from the measuring center.

The design center is in charge of a design stage of a dental prosthesis, which is the most difficult in the CAD/CAM system. Accordingly, the design center is provided with at least facilities for the design processing and employs experts having a skilled knowledge and technique for dental techniques as well as having a sufficient knowledge and technique for a CAD design. And, on a basis of the measure data sent from the measuring center, the design center carries out design processing of a dental prosthesis, which will be a shape of an ideal dental prosthesis, based on the three-dimensional graphic of the intra-oral shape displayed on a graphic display device such as a CRT (cathode ray tube) screen of a computer.

Specifically, first of all, the three-dimensional graphic of the shape of the abutment tooth is displayed on the graphic display device, and if desired, the shape of the adjacent teeth or antagonists of the abutment tooth is subjected to three-dimensional graphic display. At this time, it is preferred to previously store rough shape information regarding the desired dental prosthesis within a data base of a computer and take out the information from the data base at need, thereby synthesizing it with the shape information regarding the abutment tooth (No. 6 in the left side of the mandibula, in the above-described case) on a screen. As the rough shape information regarding the dental prosthesis, stored is a standard shape of a tooth of human beings. The standard shape of a tooth may be a standard shape of every dental site. Further, it is preferred to add information regarding the shape that varies depending on the age, sex, etc. Also, shape information of a tooth of a patient himself or herself at the time of healthy state can be used. In the case of a crown, the positional relation is displayed in three-dimensional graphic on a graphic display device, an arbitrary crown shape is designed such that it is accommodated in a space between the both, the occlusal relation is simulated on the graphic display device to adjust the relation with antagonists such as a contact point, thereby determining the crown shape. Further, in the case where the dental prosthesis is a bridge, it is necessary to design a deficient tooth portion, too. In this case, a contact point is provided at an arbitrary position of a visible outline of the crown positioned in the both sides of the deficient tooth portion as designed by the foregoing method, and the deficient tooth portion (pontic portion) having a proper size is designed. Then the relation with the antagonist is adjusted and direction of mounting/dismounting is confirmed on the graphic display so as to determine the shape of a bridge. Moreover, it is possible to impart a fissure in enamel to the dental prosthesis, or to deform the dental prosthesis, at need. Incidentally, during designing the dental prosthesis, when a standard data regarding a bridge as registered previously is used, the design may proceed with ease. In addition, in the case where the dental prosthesis is applied to anterior teeth or the like and is required to have aesthetics, as a matter of course, the design may be carried out in such a manner that an offset is made corresponding to a certain thickness, so as to prepare a labial portion or occlusal portion or the like of the dental prosthesis using a crown resin, a porcelain veneer, etc.

Next, carried out are a design operation for making a margin of the dental prosthesis coincide with a margin line of the abutment tooth and a design operation for securing a cement space in the dental prosthesis. Specifically, the design is carried out such that a visible outline of the margin of the dental prosthesis is deformed based on the shape of the abutment tooth with respect to the dental prosthesis displayed in three-dimensional graphic on the graphic display device, thereby making the margin of the dental prosthesis coincide with the margin line of the abutment tooth. Thereafter, in order to secure a cement layer, the design is carried out in such a manner that an offset is made corresponding to a certain site and thickness. Incidentally, with respect to the certain site and thickness for securing the cement layer, preferred are a site positioned above the margin portion by about 0.2 to 2 mm and a thickness of about 20 to 150 $\mu$m generally. When the shape of the dental prosthesis has been determined, a quality, a size, etc. of a block material to be processed are set up on the graphic display device, and a rest, which will be a support portion during the processing, is added on the display device. The rest is corresponding to a sprue line of the casting and displayed in a cylindrical shape in a three-dimensional graphic manner on the graphic display device. And, the movement, the rotation and the change of diameter are carried out using a device such as a mouse, and the rest is set up at an optimum position from the viewpoint of the shape while avoiding the occlusal surface and the margin portion. Thereafter, the size of the material as set up by means of automatic processing by a computer is compared with the size of the dental prosthesis to be prepared. In the case where the dental prosthesis as designed is larger than the material to be used, the position of the rest to be set up is changed, or the material that is intended to use is changed to one having a larger size. Thus, after the conditions for designing the dental prosthesis have been determined, ultimate automatic computation by the computer (so-called computation of CAD) is carried out. The design data as the result of the computation is stored in a memory within a computer, or an external preservation medium such as a floppy disc and an MO disc, as a digital signal.

The thus obtained design data is sent to a processing center from the design center utilizing communication means such as E-mail and Internet. At the time of sending the design data, it is preferred that information on the shape, color tone, model number, etc. regarding the block material to be used is sent simultaneously. As described, since an expert at the design center carries out the design stage of a dental prosthesis, which is the most difficult in the CAD/CAM system, the design of a dental prosthesis in an ideal form and with a superior fitness precision can be carried out efficiently.

The processing center is provided with at least a milling processor of a CAD/CAM system. The design data sent from the design center is transmitted as a processing command to an NC (numerical control) milling processor. Simultaneously, the block material to be used is chosen and installed in an automatic milling processor, and then subjected to milling processing based on the design data from the design center using a milling tool such as a diamond bar and a carbide bar, to prepare the dental prosthesis. In the case where a plaster model is used, the prepared dental prosthesis is sent to the measuring center and set on the first measured plaster model, and is then returned to the dental office.

In the preparation process of the dental prosthesis according to the present invention, in the case where the both apparatus of the measuring instrument of the CAD/CAM system and the milling processor are provided in the same dental laboratory or the like, as a matter of course, the processing center and the measuring center may be located in the same facility.

As described above in detail, the process for preparing a dental prosthesis according to the present invention is concerned with the preparation of a dental prosthesis using a CAD/CAM system, in which an expert at the design center is in charge of the design stage of a dental prosthesis, which is the most difficult in the CAD/CAM system, with utilizing communication means, thereby enabling to prepare a dental prosthesis in an ideal form and with a superior fitness precision. Thus, the process for a dental prosthesis having the various advantages as described according to the present invention is greatly valuable in contribution to the dental field.

While the invention has been described in detail and with reference to specific embodiments thereof, it will be apparent to one skilled in the art that various changes and modifications can be made therein without departing from the spirit and scope thereof.

What is claimed is:

1. A process for preparing a dental prosthesis utilizing a CAD/CAM system, comprising the steps of:

preparing a plaster model by impression taking within the oral cavity of a patient at a dental office;

delivering the plaster model to a measuring center;

at the measuring center, storing as a first digital signal, three-dimensional coordinate information of an intra-oral shape measured on a basis of the plaster model;

sending the obtained measured data to a design center using a first communication apparatus;

at the design center, reproducing the intra-oral shape on a graphic display device based on the received measured data as a three-dimensional graphic, designing a shape of a dental prosthesis and storing that shape as a second digital signal, and then sending the obtained design data of the dental prosthesis to a processing center using a second communication apparatus;

at the processing center, transmitting the received design data to a milling processor as a processing command to subject a block material to milling processing to prepare a dental prosthesis;

delivering the dental prosthesis to the measuring center;

comparing the dental prosthesis with the plaster model at the measuring center by setting the dental prosthesis on the plaster model; and returning the dental prosthesis and the plaster model to the dental office.

* * * * *